United States Patent
Foley et al.

(10) Patent No.: US 11,926,577 B2
(45) Date of Patent: Mar. 12, 2024

(54) METHOD FOR SYNTHESIS OF 2-METHYL-2-HYDROXYHEPTANE AND 2-METHYL 2-ALKOXYHEPTANES

(71) Applicant: P2 Science, Inc., Woodbridge, CT (US)

(72) Inventors: Patrick Foley, New Haven, CT (US); Yonghua Yang, East Lyme, CT (US); Yong Tu, Cheshire, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 17/758,053

(22) PCT Filed: Oct. 8, 2021

(86) PCT No.: PCT/US2021/054278
§ 371 (c)(1),
(2) Date: Jun. 27, 2022

(87) PCT Pub. No.: WO2022/076892
PCT Pub. Date: Apr. 14, 2022

(65) Prior Publication Data
US 2023/0065920 A1    Mar. 2, 2023

Related U.S. Application Data

(60) Provisional application No. 63/089,579, filed on Oct. 9, 2020.

(51) Int. Cl.
*C07C 29/04*    (2006.01)
*C07C 1/32*    (2006.01)
*C07C 29/80*    (2006.01)
*C07C 41/06*    (2006.01)
*C07C 249/16*    (2006.01)

(52) U.S. Cl.
CPC .............. *C07C 29/04* (2013.01); *C07C 1/323* (2013.01); *C07C 29/80* (2013.01); *C07C 41/06* (2013.01); *C07C 249/16* (2013.01)

(58) Field of Classification Search
CPC ..... C07C 29/04; C07C 31/125; C07C 249/16; C07C 251/78

USPC .......................................................... 568/885
See application file for complete search history.

(56) References Cited

U.S. PATENT DOCUMENTS 2,019,762 A    9/1935    Moravec et al.
2019/0177653 A1    6/2019    Lombardo et al.

FOREIGN PATENT DOCUMENTS

WO    WO 2016/105449    6/2016

OTHER PUBLICATIONS

Hurkes, et al., "Silanol-Based Surfactants: Synthetic Access and Properties of an Innovative Class of Environmentally Benign Detergents", *Chemistry—A European Journal*, 20(30), pp. 9330-9335, (2014).
Luyben, W. L., "Design and Control of the Methoxy-Methyl-Heptane Process", *Indus. & Engin. Chem. Res.*, 49(13), pp. 6164-6175, (2010).
Mitani, et al., "Studies on Regioselective Addition of Alkyl(phosphine)copper Complexes to Epoxides", *J. Chem. Res. Synop.*, vol. 9, pp. 498-499, (1998).
Parquet, et al., "Microwave-Assisted Wolff-Kishner Reduction Reaction", *Journal of Chemical Education*, 74(10), pp. 1225, (1997).
Reetz, et al., "CH3Li/TiC14: A Non-Basic and Highly Selective Grignard Analogue", *Tetrahedron*, 42(11), pp. 2931-2935, (1986).
Huang-Minlon, "Reduction of Steroid Ketones and other Carbonyl Compounds by Modified Wolff-Kishner Method", *Journal of the American Chemical Society*, 71(10), pp. 3301-3303, (1949).
Ramaswami, et al., "Terpenoids. IL. A Study of the Prins Reaction on the Isopropylidene-Type Double Bonds", *The Journal of Organic Chemistry, American Chemical Society.*, 29(8), pp. 2245-2248, (1964).

*Primary Examiner* — Ana Z Muresan
(74) *Attorney, Agent, or Firm* — Hoxie & Associates LLC

(57) ABSTRACT

The present disclosure pertains to a new synthetic method for the preparation of 2-methyl-2-hydroxyheptane and 2-methyl-2-alkoxyheptanes, which are valuable commodities for use in flavors, fragrances and various personal care products, such as cosmetics.

26 Claims, No Drawings

METHOD FOR SYNTHESIS OF 2-METHYL-2-HYDROXYHEPTANE AND 2-METHYL 2-ALKOXYHEPTANES

CROSS-REFERENCE TO RELATED APPLICATIONS

This Application is a national stage entry filed under 35 U.S.C. § 371 of PCT international application No. PCT/US2021/054278, filed on Oct. 8, 2021, which claims priority to, and the benefit of, U.S. Provisional Application Ser. No. 63/089,579, filed on Oct. 9, 2020, the contents of each of which are hereby incorporated by reference in their entireties.

FIELD OF INVENTION

The present disclosure pertains to a new synthetic method for the preparation of 2-methyl-2-hydroxyheptane and 2-methyl-2-alkoxyheptanes, which are valuable commodities for use in flavors, fragrances and various personal care products, such as cosmetics.

BACKGROUND

2-Hydroxy-2-methyl heptane, hereinafter referred to as Compound 1-A, has the following structure:

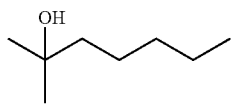

1-A

Compound 1-A has a strong odor reminiscent of pine and/or muguet. It has proven very useful as a flavor or fragrance ingredient because of its appealing smell, volatility, and strength of smell (enabling its use at low concentrations).

Related $C_{1-4}$ alkyl ethers of Compound 1-A are also highly useful as flavor and fragrance ingredients, such as Compounds 1-B and 1-C below:

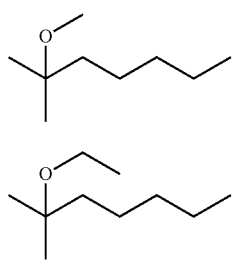

1-B

1-C

Various syntheses of Compound 1-A have been reported, with many variations on the starting material. For example, Hurkes et al., report the addition of pentyl magnesium bromide to acetone. *Chemistry—A European Journal*, 20(30):9330-35 (2014). Reetz et al. report the addition of methyllithium to 2-heptanone with titanium tetrachloride. *Tetrahedron*, 42(11):2931-5 (1986). Ritani et al. report the addition of butyl magnesium bromide to 2,2-dimethyloxirane in the presence of copper bromide and triphenylphosphine. *J. Chem. Res. Synop.* 9:498-499, 2201-16 (1998).

Each of these reactions suffers from various drawbacks, especially the use of highly toxic and reactive reagents (organometallic reagents and titanium reagents). Organometallic reagents are particularly disadvantageous in large scale industrial use because of their water sensitivity and the risk of creation of flammable gas mixtures. Methyllithium, butyl magnesium bromide and pentyl magnesium bromide for example, react with water or moisture to form methane, butane, or pentane gas, respectively. Titanium tetrachloride reacts with water to form an acidic cloud of titanium oxides and hydrochloric acid. These reagents are also relatively expensive. In addition, these reactions typically require the use of environmentally unsafe solvents, such as dialkyl ethers and tetrahydrofuran.

Compound 1-B has been reported to be made under high pressure, high temperature conditions by reacting 2-methyl-1-heptene with methanol at, for example, 400 Kelvin and 12 atmospheres. Luyben, W. L., *Indus. & Engin. Chem. Res.*, 49(13):6164-75 (2010). Such conditions require specialized reactors and other equipment, as well as presenting a significant hazard and risk of explosion.

Thus, there is a need for improved methods for the synthesis of Compound 1-A, and $C_{1-4}$ alkyl ethers thereof, which rely on less hazardous, less costly and/or less toxic reagents, as well as a need for obtaining the highest yields using the least expensive starting materials.

BRIEF SUMMARY

Applicants have discovered a much-improved, economically feasible and relatively safe method for the synthesis of 2-methyl-2-heptanol (Compound 1-A) and $C_{1-4}$ alkyl ethers thereof. The present disclosure provides a method of making 2-methyl-2-heptanol (Compound 1-A) and $C_{1-4}$ alkyl ethers thereof comprising the step of reacting 2-methyl-2-heptene (Compound 2) with water, or a $C_{1-4}$ alcohol, in the presence of an acid to form Compound 1 or a $C_{1-4}$ alkyl ether thereof. In some embodiments, the disclosure further provides a method of reacting 6-methyl-5-hepten-2-one (Compound 3) with a hydrazine compound to form an intermediate hydrazone (Compound 3-A), followed by base-catalyzed reduction of the hydrazone to form Compound 2.

DETAILED DESCRIPTION

Applicants have discovered a much-improved, economically feasible and relatively safe method for the synthesis of 2-methyl-2-heptanol (Compound 1-A) and $C_{1-4}$ alkyl ethers thereof. The method involves the use of relatively inexpensive and safe reagents compared to prior art methods, and results in good yields for high cost effectiveness.

In a first aspect, the present disclosure therefore provides, a method (Method 1) of making Compound 1 comprising reacting Compound 2 with water or a $C_{1-4}$ alcohol, in the presence of an acid:

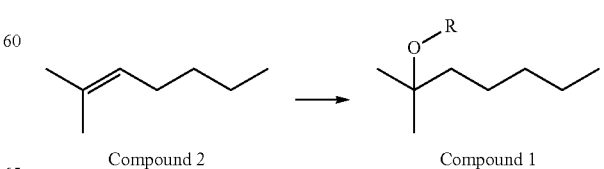

Compound 2           Compound 1 wherein R is H or $C_{1-4}$ alkyl (e.g., methyl or ethyl).

In further embodiments of the first aspect, the present disclosure provides:

1.1 Method 1, wherein R is H;
1.2 Method 1, wherein R is $C_{1-4}$ alkyl (e.g., methyl or ethyl);
1.3 Method 1 or 1.1, wherein Compound 2 is reacted with water;
1.4 Method 1 or 1.2, wherein Compound 2 is reacted with a $C_{1-4}$ alcohol (e.g., methanol or ethanol);
1.5 Method 1 or any of Methods 1.1-1.4, wherein the acid is present in a catalytic amount (e.g., up to 0.5 equivalents based on the amount of Compound 2);
1.6 Method 1 or any of Methods 1.1-1.4, wherein the acid is present in an amount of 0.01 to 0.25 equivalents based on the amount of Compound 2, e.g., 0.01 to 0.15 equivalents, or 0.01 to 0.10 equivalents, or 0.01 to 0.05 equivalents, or 0.01 to 0.01 equivalents;
1.7 Method 1.1 or 1.4, wherein the acid is dissolved in a solvent comprising water (e.g., at a concentration of less than 30 wt %, e.g., at 1 to 30% or 1 to 20%, or 1 to 10% w/w), and wherein the Compound 2 is added to the solution of the acid in water;
1.8 Method 1 or any of Methods 1.1-1.4, wherein the acid is a substantially pure acid or a concentrated solution of the acid (e.g., greater than 50 wt %);
1.9 Method 1, or any of Methods 1.1-1.8, wherein the acid is selected from sulfuric acid, nitric acid, hydrochloric acid, phosphoric acid, and perchloric acid;
1.10 Method 1.9, wherein the acid is selected from sulfuric acid, nitric acid and hydrochloric acid;
1.11 Method 1.9 or 1.10, wherein the acid is in concentrated form (e.g., 30-99% sulfuric acid, 20-38% hydrochloric acid, or 30-68% nitric acid, or 70 to 85% phosphoric acid);
1.12 Method 1.11, wherein the acid is concentrated sulfuric acid (e.g., 30-99% w/w sulfuric acid, such as 62-99% or 78-99% or 93-99% or about 98% w/w);
1.13 Any one of Methods 1.8-1.12, wherein the acid is the solvent (e.g., the solvent is concentrated sulfuric acid), without any additional solvent (e.g., water or ice or $C_{1-4}$ alcohol);
1.14 Any one of Methods 1.8-1.12, wherein the solvent is the acid diluted with a volume of water or ice or $C_{1-4}$ alcohol (e.g., in a 2:1 to 1:2 v/v ratio of the acid to the water and/or ice or alcohol, such as 1.5:1 to 1:1, or 1.15:1 to 1:1, or about 1.1:1 or about 1:1 v/v);
1.15 Method 1.14, wherein the acid is diluted with water and/or ice or $C_{1-4}$ alcohol, followed by addition of the Compound 2;
1.16 Method 1 or any of Methods 1.1-1.5, wherein the acid is a solid resin-bound acid, such as an Amberlyst®-type acidic resin (e.g., macroreticular or cellular resins or silica covalently bonded to sulfonic acid or carboxylic acid groups), and wherein the Compound 2 is combined with the solid resin-bound acid in a suitable solvent (e.g., water, a $C_{1-4}$ alcohol, or a polar aprotic solvent, such as acetonitrile, or a combination thereof);
1.17 Method 1, or any one of Methods 1.1-1.16, wherein the method comprises adding the Compound 2 to the acid or acid mixture;
1.18 Any one of Methods 1.8-1.17, wherein the method comprises diluting the acid with water and/or ice or $C_{1-4}$ alcohol (e.g., at a 2:1-1:2 v/v ratio), followed by adding the Compound 2;
1.19 Any one of Methods 1.1-1.18, wherein the acid is concentrated sulfuric acid (e.g., about 98% w/w sulfuric acid), and the acid is diluted with water and/or ice or $C_{1-4}$ alcohol (e.g., at a 1.5:1 to 1:1 v/v ratio of acid to water and/or ice or $C_{1-4}$ alcohol, or 1.15:1 to 1:1, or about 1.1:1 or about 1:1 v/v), followed by addition of the Compound 2;
1.20 Method 1, or any one of Methods 1.1-1.19, wherein the reaction temperature is maintained at or below 25° C., e.g., at −10 to 25° C., or at −10 to 20° C., or at −5 to 15° C., or at 0 to 10° C., or at 0 to 8° C., or a combination thereof;
1.21 Method 1, or any one of Methods 1.1-1.20, wherein the reaction is conducted for less than 24 hours, e.g., less than 12 hours, or less than 8 hours, or 0.5 to 6 hours, or 0.5 to 4 hours, said time being inclusive of any time spent adding the Compound 2 to the acid mixture (e.g., 0.1 to 3 hours for addition, or 0.5 to 1.5 hours, or 1 to 1.5 hours);
1.22 Method 1, or any of one of Methods 1.1-1.22, wherein the product is isolated by extraction of the organic layer, washing with aqueous base, drying to remove residual water, and distillation to purify the product.
1.23 Method 1, or any one of Methods 1.1-1.23, wherein the method further comprises the step of converting Compound 3 to Compound 2, followed by the conversion of Compound 2 to Compound 1, as described hereinabove.
1.24 Method 1.23, wherein the step of converting Compound 3 to Compound 2 is carried out as described in Method 2 or any of methods 2.1 et seq.

In a second aspect, the present disclosure provides, a method (Method 2) of making Compound 2 comprising the steps of (A) reacting Compound 3 with a hydrazine compound to form intermediate Compound 3-A, followed by (B) base-catalyzed reduction of the hydrazone to form Compound 2:

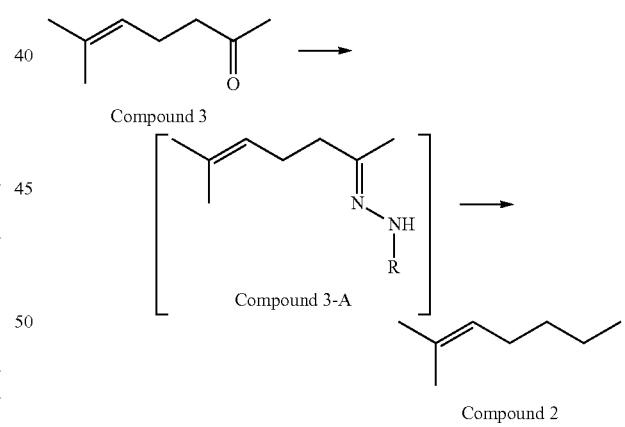

In further embodiments of the second aspect, the present disclosure provides:

2.1 Method 2, wherein the hydrazine compound is hydrazine or a hydrate thereof or an N-alkyl, N-aryl (e.g., N-phenylhydrazine), N-alkylsulfonyl, or N-arylsulfonyl hydrazine (e.g., N-tosylhydrazine);
2.2 Method 2.1, wherein the hydrazine compound is hydrazine (e.g., hydrazine monohydrate or anhydrous hydrazine);
2.3 Method 2 or any one of Methods 2.1-2.2, wherein the hydrazine compound is present in an amount of 0.9 to 5 equivalents based on the amount of Compound 3, e.g., 0.95 to 3 equivalents, or 0.95 to 2 equivalents, or 0.95 to 1.5 equivalents, or 0.95 to 1.3 equivalents, or 1.1-1.5 equivalents, or 1.2-1.4 equivalents, or about 1.3 equivalents;

2.4 Method 2, or any one of Methods 2.1-2.3, wherein the hydrazine compound is added to the Compound 3 under neat conditions (no additional solvent present);

2.5 Method 2, or any one of Methods 2.1-2.3, wherein Compound 3 is added to the hydrazine compound under neat conditions (no additional solvent present);

2.6 Method 2, or any one of Methods 2.1-2.3, wherein the hydrazine compound is added to a solution or suspension of the Compound 3 in a suitable solvent (e.g., a nonpolar solvent or a polar aprotic solvent);

2.7 Method 2, or any of Methods 2.1-2.6, wherein the R group of Compound 3 is selected from $C_{1-6}$ alkyl, optionally substituted aryl, optionally substituted heteroaryl, and H;

2.8 Method 2.7, wherein R is H;

2.9 Method 2 or any one of methods 2.1-2.8, wherein the Compound 3 is added to neat hydrazine monohydrate;

2.10 Method 2, or any one of Methods 2.1-2.9, wherein step (A) is carried out for less than 24 hours, e.g., less than 12 hours, or less than 9 hours, or less than 6 hours, or less than 3 hours, or less than 2 hours, or about 1 hour;

2.11 Method 2, or any one of Methods 2.1-2.10, wherein the reaction temperature of step (A) is maintained at or below 25° C., e.g., at −10 to 25° C., or at −10 to 20° C., or at −5 to 15° C., or at −5 to 10° C., or at −5 to 5° C., or about 0° C. or about 25° C., or a combination thereof;

2.12 Method 2 or any one of Methods 2.1-2.11, wherein intermediate Compound 3-A is not isolated;

2.13 Method 2 or any one of Methods 2.1-2.11, wherein intermediate Compound 3-A is isolated in crude form from step (A), e.g., by organic/aqueous extraction;

2.14 Method 2 or any one of Methods 2.1-2.13, wherein the base of step (B) is a hydroxide or alkoxide base;

2.15 Method 2, or any one of Methods 2.1-2.14, wherein step (B) comprises treating intermediate Compound 3-A with the base in a suitable solvent (e.g., in an alcohol, polar protic solvent or polar aprotic solvent);

2.16 Method 2 or any one of Methods 2.1-2.15, wherein the base for step (B) is a lithium, sodium, or potassium alkoxide (e.g., of a $C_{1-4}$ alcohol or $C_{1-4}$ diol);

2.17 Method 2.16, wherein the lithium, sodium, or potassium alkoxide is formed in-situ by adding lithium, sodium or potassium metal to the corresponding alcohol as the suitable solvent (e.g., a $C_{1-4}$ alcohol or $C_{1-4}$ diol);

2.18 Method 2.16 or 2.17, wherein the base is lithium, sodium, or potassium methoxide, ethoxide, propoxide, isopropoxide, n-butoxide or t-butoxide, and/or the alcohol is methanol, ethanol, propanol, isopropanol, n-butanol, tert-butanol, ethylene glycol, 1,2-propylene glycol, or 1,3-propylene glycol, or a mixture thereof;

2.19 Method 2.14 or 2.15, wherein the base is lithium hydroxide, sodium hydroxide, or potassium hydroxide;

2.20 Any one of Methods 2.15 to 2.20, wherein the suitable solvent is water, methanol, ethanol, propanol, isopropanol, n-butanol, tert-butanol, ethylene glycol, 1,2-propylene glycol, or 1,3-propylene glycol, or a mixture thereof;

2.21 Method 2.20, wherein the base is potassium hydroxide and the solvent is water, methanol, ethanol, ethylene glycol or a mixture thereof;

2.22 Method 2.21, wherein the base is potassium hydroxide and the solvent is ethylene glycol;

2.23 Any one of methods 2.15-2.22, wherein the method comprises adding the Compound 3-A to the mixture of base in suitable solvent;

2.24 Any one of methods 2.15-2.22, wherein the method comprises adding the base to the Compound 3-A in suitable solvent;

2.25 Method 2, or any one of 2.1-2.24, wherein step (B) comprises the use of 0.1 to 3 equivalents of base compared to the amount of Compound 3 or compared to the amount of Compound 3-A, e.g., 0.1 to 2.0 equivalents, or 0.1 to 1.5 equivalents, or 0.1 to 1 equivalent, or 0.1 to 0.7 equivalents, or 0.1 to 0.5 equivalents or 0.1 to 0.3 equivalents, or 0.2 to 0.3 equivalents, or about 0.25 equivalents;

2.26 Method 2, or any one of Methods 2.1-2.25, wherein intermediate Compound 3-A and the mixture of base and solvent are combined at a temperature of 20° C. or above, e.g., at 25 to 100° C., or at 40 to 75° C., or at 50 to 70° C., or at about 60° C., followed by heating to the reaction temperature;

2.27 Method 2, or any one of Methods 2.1-2.26, wherein intermediate Compound 3-A and the mixture of base and solvent are combined at the reaction temperature (e.g., the Compound 3-A is added to the mixture of base in suitable solvent at the reaction temperature, or the base is added to the mixture of Compound 3-A and suitable solvent at the reaction temperature);

2.28 Method 2, or any one of Methods 2.1-2.27, wherein the reaction temperature of step (B) is maintained at above 50° C., e.g., at 50 to 300° C., or at 75 to 300° C., or at 100 to 250° C., or at 125 to 200° C., or at 150 to 175° C.;

2.29 Method 2, or any one of Methods 2.1-2.28, wherein the reaction temperature of step (B) is maintained at or about at the boiling point of the solvent (e.g., at +/−5° C. of the boiling point);

2.30 Method 2, or any one of Methods 2.1-2.28, wherein the step (B) reaction is conducted for less than 24 hours, e.g., less than 12 hours, or less than 8 hours, or 0.5 to 6 hours, or 1 to 4 hours, exclusive of the time spent heating to the reaction temperature;

2.31 Method 2, or any of one of Methods 2.1-2.30, wherein the product is isolated by extraction of the organic layer, washing with aqueous acid, drying to remove residual water, and distillation to purify the product;

2.32 Method 2, or any of one of Methods 2.1-2.30, wherein the product is isolated by continuous distillation from the reaction mixture;

2.33 Method 2.32, wherein the distillate is collected, washed with water and/or washed with aqueous acid, dried to remove residual water, and optionally further purified (e.g., by further distillation);

2.34 Method 2, or any one of Methods 2.1-2.33, wherein the method further comprises the step of converting Compound 2 to Compound 1;

2.35 Method 2.34, wherein the step of converting Compound 1 to Compound 1 is carried out as described in Method 1 or any of methods 1.1 et seq.

In a third aspect, the present disclosure provides Compound 1 made according to Method 1 or any of 1.1 et seq.

In a fourth aspect, the present disclosure provides a product or composition, such as an organoleptic composition, comprising Compound 1, made according to Method 1 or any of 1.1 et seq. In some embodiments, the Compound 1 may be used alone as a fragrance or added into a fragrance composition and/or consumer product as an agent for increasing substantivity and/or retention of a fragrance preparation and/or as a fixative.

Suitable solvents may include, alcohols such as methanol, ethanol, propanol, isopropanol, butanol, tert-butanol and the like; lower alkyl ester of lower carboxylic acid such ethyl acetate and the like; alkane nitriles such as acetonitrile, propionitrile, butyronitrile, isobutyronitrile, valeronitrile and the like; aromatic hydrocarbons such as benzene, toluene, xylene, anisole and the like; aliphatic hydrocarbons such as heptane, octane, cyclohexane, cycloheptane, cyclooctane and the like; and water. All these solvents can be used singly or in mixture with each other. Water can also be used as a solvent with or without mixing above mentioned solvents during the reaction.

EXAMPLES

Example 1: -Methyl-2-heptene (Compound 2)

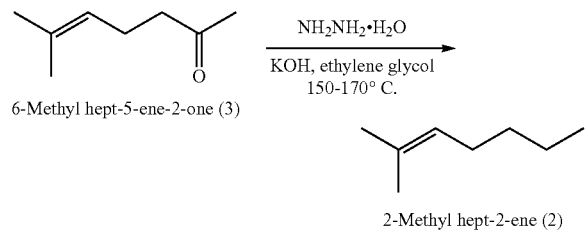

6-Methyl hept-5-ene-2-one (3, 480 g, 3.8 mol) was added dropwise to hydrazine monohydrate (247 g, 4.9 mol, 1.3 eq.) at 0° C. over 1 hour. The mixture was stirred at ambient temperature overnight. The organic layer was separated (495 g) to afford intermediate (6-methylhept-5-en-2-ylidene)hydrazine (3-A). From this, 250 g of the intermediate was added into a solution of potassium hydroxide (56 g, 1 mol) in diethylene glycol at 60° C. The mixture was slowly heated to 156-170° C. and stirred for 3 hours while Compound 2 was distilled out. The remaining above intermediate 3-A (245 g) was slowly added at 160-166° C. and more product (2) was distilled out in the process. All of the fractions of product 2 were collected and washed with water (2×), 0.5 N HCl and brine. Dried with anhydrous $Na_2SO_4$, and distilled to afford 2 (273.1 g, 64%).

Example 2: 2-Methyl-2-heptanol (Compound 1-A)

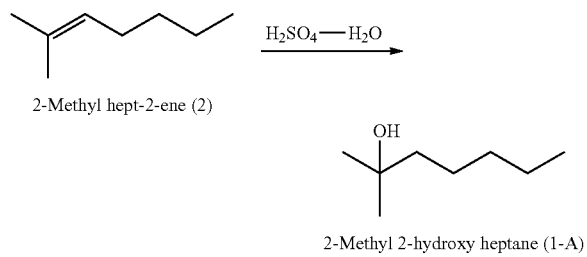

Concentrated sulfuric acid (160 ml; about 294 g) was slowly added to ice (130 g, about 142 mL). The mixture was cooled in an ice-water bath. Then Compound 2 (110 g) was added dropwise over 80 minutes and the internal temperature was controlled at 0 to 8° C. The mixture was stirred for another two hours and the internal temperature was maintained below 5° C. The mixture was diluted with 400 ml of cold water and stirred overnight. The organic layer was separated, washed with NaOH (1N, 2×30 ml) and brine (30 ml). The resulting organic layer was dried with anhydrous $Na_2SO_4/K_2CO_3$, distilled under vacuum to afford the product 1-A as colorless liquid (82.1 g, 64%, purity >99%). NMR and GC were identical with authentic sample.

Example 2: 2-Methyl-2-methoxy heptane (Compound 1-B)

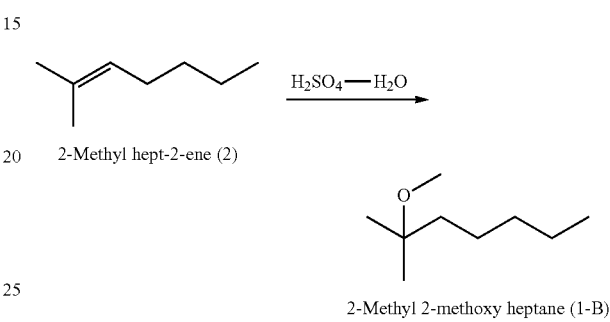

2-Methyl-2-heptene (52 g, 0.46 mol) was slowly added to a solution of concentrated $H_2SO_4$ (12.3 ml, 0.23 mol) in MeOH (110 ml) at 35° C., over 0.5 hours under nitrogen. The mixture was stirred at 35° C. for 6 hours, then was cooled down and the methanol layer was separated, washed with 1N NaOH (2×30 ml), washed with brine (30 ml), and dried over sodium sulfate. The crude product was distilled under vacuum to afford the product as a colorless liquid (9.7 g).

The Examples provided herein are exemplary only and are not intended to be limiting in any way to the various aspects and embodiments of the invention described herein.

We claim:

1. A method of making 2-methyl-2-heptanol or a $C_{1-4}$ alkyl ether thereof (Compound 1) comprising the steps of:
   (A) reacting 6-methyl-5-hepten-2-one (Compound 3) with a hydrazine compound to form an intermediate hydrazone Compound 3-A;
   (B) base-catalyzed reduction of the hydrazone to form Compound 2:

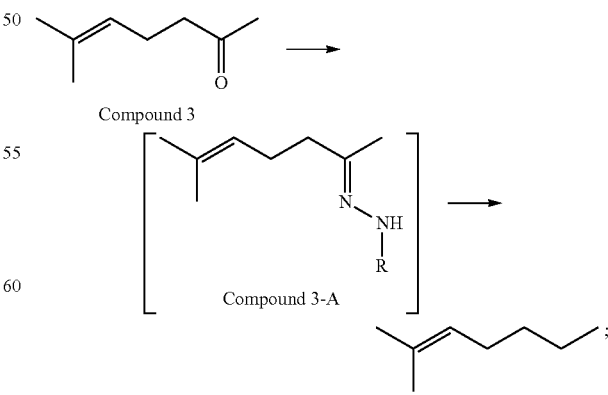

and (C) reacting the 2-methyl-2-heptene (Compound 2) with water or a $C_{1-4}$ alcohol in the presence of an acid to form Compound 1:

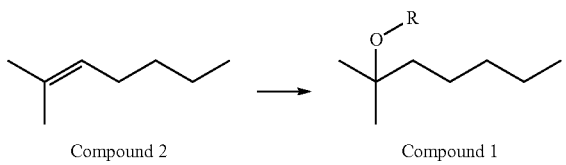

Compound 2        Compound 1 wherein R is H or $C_{1-4}$ alkyl.

2. The method of claim 1, wherein R is H, and the Compound 2 is reacted with water.

3. The method of claim 1, wherein R is $C_{1-4}$ alkyl, and the Compound 2 is reacted with a $C_{1-4}$ alcohol.

4. The method of claim 1, wherein the acid is present in an amount of 0.01 to 0.25 equivalents based on the amount of Compound 2.

5. The method of claim 1, wherein the acid is a substantially pure acid or a concentrated solution of the acid.

6. The method of claim 1, wherein the acid is selected from the group consisting of sulfuric acid, nitric acid, hydrochloric acid, phosphoric acid, and perchloric acid.

7. The method of claim 6, wherein the acid is concentrated sulfuric acid.

8. The method of claim 1, wherein the acid is concentrated sulfuric acid, and the acid is diluted with water and/or ice or $C_{1-4}$ alcohol, followed by addition of the Compound 2.

9. The method of claim 1, wherein the reaction temperature of step (C) is maintained at or below 25° C.

10. The method of claim 1, wherein the reaction of step (C) is conducted for less than 24 hours, said time being inclusive of any time spent adding the Compound 2 to the acid mixture.

11. The method of claim 1, wherein the product of step (C) is isolated by the steps of extraction of the organic layer, washing with aqueous base, drying to remove residual water, and distillation to purify the product.

12. The method of claim 1, wherein the hydrazine compound is selected from the group consisting of hydrazine, a hydrazine hydrate, an N-alkyl, N-aryl hydrazine, an N-alkylsulfonyl hydrazine, and an N-arylsulfonyl hydrazine.

13. The method of claim 12, wherein the hydrazine compound is hydrazine monohydrate or anhydrous hydrazine.

14. The method of claim 1, wherein the hydrazine compound is present in an amount of 0.9 to 5 equivalents based on the amount of Compound 3.

15. The method of claim 1, wherein Compound 3 is added to the hydrazine compound under neat conditions.

16. The method of claim 1, wherein step (B) comprises treating intermediate Compound 3-A with the base in a suitable solvent.

17. The method of claim 1, wherein the base for step (B) is a lithium, sodium, or potassium alkoxide.

18. The method of claim 1, wherein the base for step (B) is selected from the group consisting of lithium hydroxide, sodium hydroxide, and potassium hydroxide.

19. The method of claim 16, wherein the suitable solvent for step (B) is selected from the group consisting of water, methanol, ethanol, propanol, isopropanol, n-butanol, tert-butanol, ethylene glycol, 1,2-propylene glycol, 1,3-propylene glycol, and a mixture thereof.

20. The method of claim 19, wherein the base is potassium hydroxide and the solvent is ethylene glycol.

21. A method of making 2-methyl-2-heptene (Compound 2) comprising the steps of (A) reacting 6-methyl-5-hepten-2-one (Compound 3) with a hydrazine compound to form an intermediate hydrazone, followed by (B) base-catalyzed reduction of the hydrazone to form Compound 2.

22. The method of claim 1, wherein R is methyl or ethyl and the Compound 2 is reacted with methanol or ethanol.

23. The method of claim 8, wherein the acid is concentrated sulfuric acid, and the acid is diluted with water and/or ice or $C_{1-4}$ alcohol at a 1.5:1 to 1:1 v/v ratio of acid to water and/or ice or $C_{1-4}$ alcohol, followed by addition of the Compound 2.

24. The method of claim 12, wherein the hydrazine compound is selected from the group consisting of hydrazine, a hydrazine hydrate, N-phenylhydrazine, and N-tosylhydrazine.

25. The method of claim 1, wherein in step (A) the Compound 3 is reacted with 0.95 to 2 equivalents of hydrazine monohydrate, and wherein in step (B) the intermediate Compound 3-A is treated with a base selected from the group consisting of lithium hydroxide, sodium hydroxide, and potassium hydroxide in a solvent selected from the group consisting of water, methanol, ethanol, propanol, isopropanol, n-butanol, tert-butanol, ethylene glycol, 1,2-propylene glycol, 1,3-propylene glycol, and a mixture thereof.

26. The method of claim 25, wherein in step (C) the Compound 2 is reacted with concentrated sulfuric acid in water, methanol, or ethanol, and wherein the acid is present in an amount of 0.01 to 0.25 equivalents based on the amount of Compound 2.

* * * * *